(12) United States Patent
Konzelmann et al.

(10) Patent No.: US 7,661,304 B2
(45) Date of Patent: Feb. 16, 2010

(54) HEATED H$_2$ SENSOR

(75) Inventors: Uwe Konzelmann, Asperg (DE); Ulrich Wagner, Stuttgart (DE); Christoph Gmelin, Stuttgart (DE); Martin Baumann, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 30 days.

(21) Appl. No.: 11/603,453

(22) Filed: Nov. 22, 2006

(65) Prior Publication Data

US 2007/0137298 A1 Jun. 21, 2007

(30) Foreign Application Priority Data

Dec. 9, 2005 (DE) .................. 10 2005 058 832

(51) Int. Cl.
*G01F 1/68* (2006.01)

(52) U.S. Cl. ...................................... 73/204.26

(58) Field of Classification Search ............ 73/204.26, 73/204.11, 204.25, 204.27, 865.8, 865.6; 60/513, 512
See application file for complete search history.

(56) References Cited

U.S. PATENT DOCUMENTS

| 4,935,040 | A  | * | 6/1990  | Goedert ................. 73/23.22 |
| 6,098,455 | A  | * | 8/2000  | Nukui et al. ............ 73/204.26 |
| 6,978,611 | B1 | * | 12/2005 | Landis .................... 60/513 |
| 7,017,430 | B2 | * | 3/2006  | Cross et al. ............. 73/865.8 |

FOREIGN PATENT DOCUMENTS

| DE | 196 01 791 | 7/1997 |
| DE | 101 11 840 | 10/2002 |

* cited by examiner

*Primary Examiner*—Jewel Thompson
(74) *Attorney, Agent, or Firm*—Kenyon & Kenyon LLP

(57) ABSTRACT

A method and a sensor for detecting a component, in particular H$_2$, in a gaseous fluid containing multiple components. A measuring chamber, which accommodates a heatable measuring element, is implemented in a sensor. The measuring chamber is heated.

11 Claims, 2 Drawing Sheets

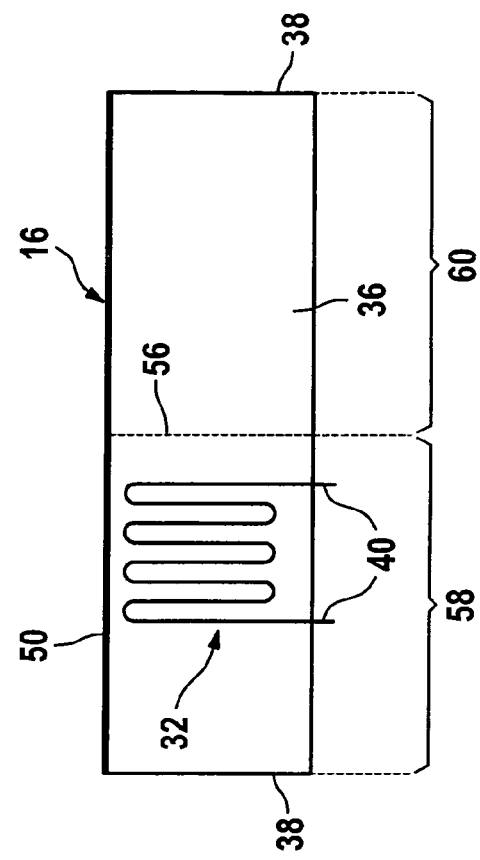
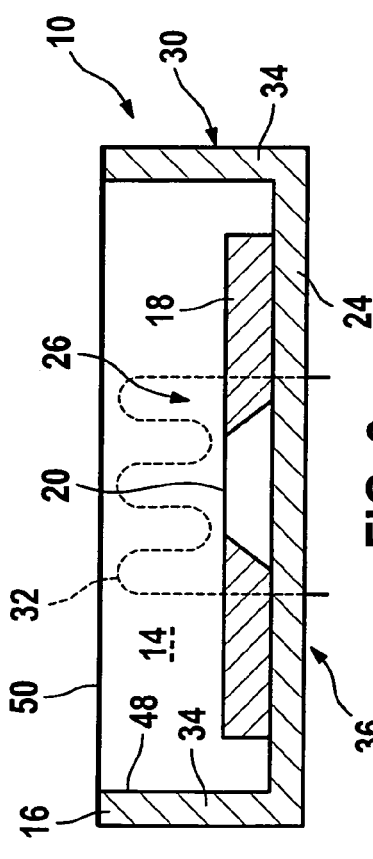
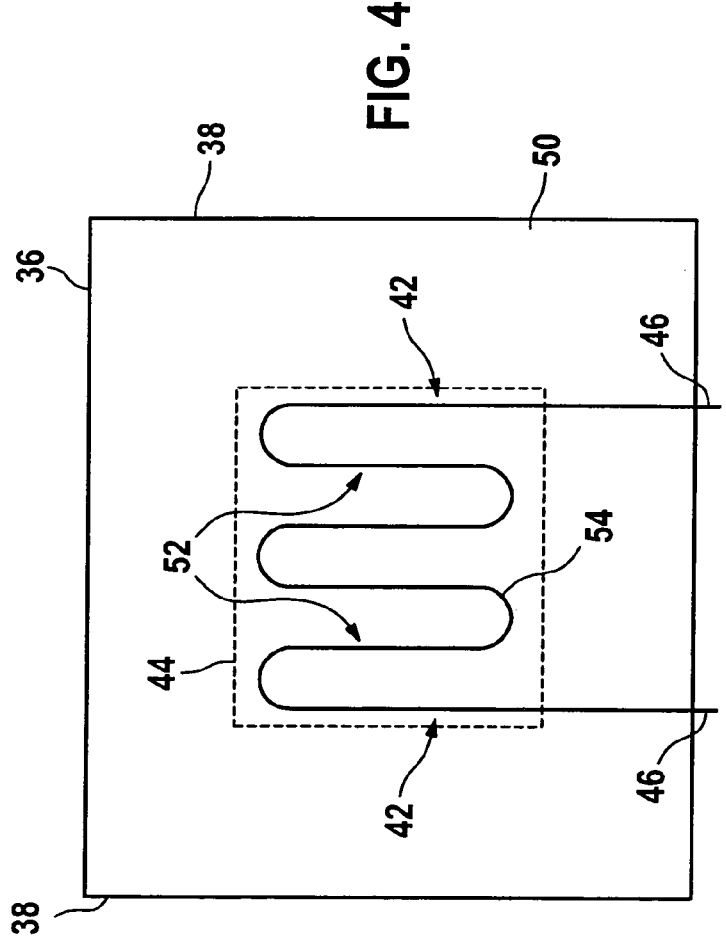

HEATED H₂ SENSOR

BACKGROUND INFORMATION

A type of sensor known from the related art is a hot-film air mass meter (HFM), an embodiment of which is described in German Patent Application No. DE 196 01 791, for example. In hot-film air mass meters of this type, a thin sensor diaphragm is typically applied to a sensor chip, which is preferably a silicon sensor chip. At least one heating resistor, which is enclosed by two or more temperature measuring resistors, is typically situated on the sensor diaphragm. The temperature distribution which may in turn be detected by the temperature measuring resistors changes in an air flow which is guided over the diaphragm. Thus, for example, an air mass flow may be determined from the resistance differential of the temperature measuring resistors. Various other variations of this sensor type are known from the related art.

A sensor chip is described in German Patent No. DE 101 11 840 which has a frame element manufactured from silicon, having a diaphragm applied thereto. Various metal webs which function as electrical heaters and/or measuring resistors are situated on the diaphragm, resulting in the area of the diaphragm forming a sensor area. Moreover, at least one auxiliary heater is additionally situated on the surface of the sensor chip and may be electrically heated in such a way that thermal gradient eddies are formed in the flowing medium in the area of the auxiliary heater, which result in deposits of contaminants in the area of the auxiliary heater beyond the sensor area and do not additionally contaminate this sensor area.

To detect hydrogen, the property of hydrogen of having significantly better thermal conductivity than air is exploited. In a sensor construction which is similar to that of the hot-film air mass meters (HFM) outlined above, an air-hydrogen mixture, for example, diffuses through a thin diaphragm or a tight grid into the measuring chamber. The presence of hydrogen changes the temperature of the heated measuring diaphragm or its thermal output, which is delivered to the surrounding air, which in turn results in the measurement signal. In these embodiment variations, the measuring chip and/or housing temperatures are typically at approximately room temperature, diaphragm temperatures typically being set between 80 K and 120 K.

This measuring method has the disadvantage that moisture contained in the gas mixture influences the thermal conductivity of an $H_2$-air mixture. At room temperature, the influence of the moisture component may be so large that detection of hydrogen in the $H_2$-air mixture is no longer possible with the required clarity.

SUMMARY OF THE INVENTION

In light of the disadvantages of the related art, an object of the present invention is to significantly reduce the influence of moisture when measuring a component of a gaseous fluid.

The present invention provides heating a measuring chamber of a housing, which accommodates a sensor for detecting a component of a gaseous fluid. In particular, the housing of the sensor and/or a cover diaphragm which covers the sensor housing is heated. The heating is performed in such a way that an excess temperature is reached which is significantly above room temperature, i.e., 25° C., thus, for example, an excess temperature of T=80° C. to 200° C. The excess temperature of a measuring diaphragm used as a measuring element is increased to an excess temperature T, preferably in the range between 100° C. and 200° C., so that the relative humidity of the fluid inside the measuring chamber of the sensor is reduced and the measurement error originating from the atmospheric moisture of the gaseous fluid is drastically reduced.

In contrast to previously known sensor embodiments, heat transmission does not occur at a temperature level between 20° C. and 120° C., but rather at a significantly elevated temperature level, thus, for example, between 80° C. and 220° C.

In one embodiment, the heating of the measuring chamber may be implemented, for example, by situating a heating resistor on at least one side of the sensor housing, which delimits the measuring chamber, the resistor running over a relatively large area on the at least one side wall of the sensor housing. In addition, it is possible to heat the housing cover, which is represented by a lid or a diaphragm, for example, from the outside using at least one further heating element, in addition to at least one side of the housing delimiting the measuring chamber. In addition to the application of the heating elements to at least one side wall of the housing of the sensor and to a lid covering the measuring chamber or a diaphragm applied to the measuring chamber, a heater of the measuring chamber may also be inserted in the side walls of the sensor housing, which delimits the measuring chamber, for detecting a component of a gaseous fluid.

Depending on the overall space available in regard to the installation location of the sensor according to the present invention, heating elements may be applied to the longitudinal sides and to the transverse sides—in the case of a rectangularly configured housing. If the sensor is implemented in the form of a flat cylinder, heating elements may be applied to the mantle surface of the flat cylinder in various peripheral angle positions.

The heating elements are preferably implemented as heating resistors, which are manufactured from a heating wire curved in a meandering shape that may be applied to a large area of the side walls of the housing of the sensor or the mantle surface of a flat housing of a sensor.

BRIEF DESCRIPTION OF THE DRAWINGS

FIG. 2 shows a side view of the sensor according to the present invention for detecting a component of a gaseous fluid.

FIG. 3 shows a view of a longitudinal side of the housing of the sensor according to the present invention.

FIG. 4 shows a top view of the housing of the sensor according to the present invention having a heating element applied to the housing top.

DETAILED DESCRIPTION

Figure 1:
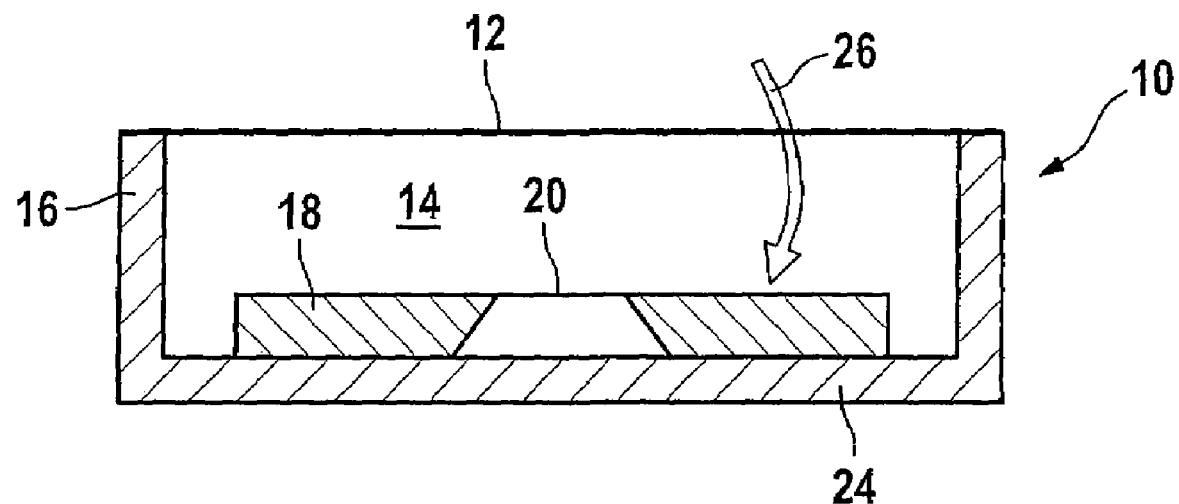
FIG. 1 shows an embodiment of a sensor known from the related art for detecting a component of a gaseous fluid.

The illustration in FIG. 1 shows a section of a sensor for detecting one component of a gaseous fluid according to the related art.

The illustration in FIG. 1 shows that a sensor 10 for detecting one component of a gaseous fluid, thus, for example, for detecting hydrogen, in a hydrogen-air-moisture mixture, includes a housing 16. Housing 16 delimits a measuring chamber 14. Sensor 10 additionally includes a chip 18 applied to a housing floor 24, which in turn contains a measuring diaphragm 20. Chip 18 is attached to housing floor 24 and is subjected to gaseous fluid 26, thus, for example, a hydrogen-air-moisture mixture 26, which diffuses through a lid 12. The temperature of chip 18 and the temperature of housing 16 of sensor 10 shown in FIG. 1 are typically in the range of room temperature, i.e., approximately 25° C. Measuring diaphragm 20 shown in the illustration of FIG. 1 is also heated and has an excess temperature T of 80 K to 120 K, in relation to the temperature of chip 18.

FIG. 2 shows housing 16 of sensor 10 according to the present invention, which is closed on top by a lid diaphragm 50.

Housing 16 includes side walls 34, which delimit measuring chamber 14. In addition, measuring chamber 14 is delimited by housing floor 24, which accommodates measuring chip 18 together with heated measuring element 20. The measuring element is understood in the following as a measuring diaphragm 20.

In the illustration of FIG. 2, housing 16 of sensor 10 has a rectangular design. The side walls, identified by reference numeral 34, may be shorter than a longitudinal side 36, as shown in FIG. 2.

A first heating element 32 is located on an external housing side 30 on the longitudinal side lying behind the sectional plane. This is advantageously implemented in a meandering manner, so that a larger area of a side wall of housing 16 extending over longitudinal side 36 may be heated. First heating element 32, shown covered in FIG. 2, may either be applied to external side 30 of housing 16 or integrated in housing 16. This may be achieved using simple manufacturing technology by extrusion coating at least one heating element 32 in a housing 16 that is injection-molded from plastic material, the heating element heating measuring chamber 14, in which heated measuring diaphragm 20 on chip 18 is embedded.

FIG. 3 shows a side view of the sensor according to the present invention from FIG. 2.

The illustration in FIG. 3 shows that first heating element 32 is applied to longitudinal side 36 of housing 16. First heating element 32 has terminals 40. In the illustration of FIG. 3, longitudinal side 36 of housing 16 is divided into a first half 58 and a second half 60. In the illustration of FIG. 3, first heating element 32 is located within first half 58 of the side wall of housing 16 extending over longitudinal side 36. The first heating element may additionally also be applied from the outside to the transverse sides of housing 16 identified by reference numeral 38. In addition to the embodiment variation of first heating element 32 as a meandering heating wire, shown in FIG. 3, planar heating may also be performed inside first half 58 or second half 60 on both sides of an axis 56, first heating element 32 also being able to be designed as a grid structure or as a planar surface, which may be applied to external side 30 of housing 16, either on a longitudinal side 36 or on a transverse side 38. Although first heating element 32 is applied to longitudinal side 36 of housing 16 in the view shown in FIG. 3, a further heating element may be applied to rear longitudinal side 36 of housing 16 (not shown in FIG. 3). In addition, it is also possible to apply a heating element from the outside to each of diametrically opposed transverse sides 38 of housing 16. While in methods known from the related art the chip temperature is approximately 20° C. and the temperature of the measuring diaphragm 20 is approximately 120° C., chip 18 in the suggested achievement of the object is operated at a significantly higher temperature level of approximately 120° C.; measuring diaphragm 20 also assumes temperatures of 180° C. to 230° C., thus, for example, a temperature of 220° C.

The illustration in FIG. 4 shows a top view of the sensor according to the present invention.

As may be inferred from the sectional illustration in FIG. 2, the top of housing 16 of sensor 10 according to the present invention is closed by a cover. The cover may be implemented as a lid diaphragm 50, which terminates measuring chamber 14 (not shown in FIG. 4 but may be inferred from FIG. 2), to allow diffusion of gaseous fluid 26, which contains multiple components. A second heating element 42, which has a meandering shape 52, is applied to lid diaphragm 50 within a central area 44. The terminals of further second heating element 42 are identified by reference numeral 46.

Second heating element 42, shown in FIG. 4, which is applied to lid diaphragm 50, has a heating wire 54. Large-area heating of central area 44 of lid diaphragm 50 may be achieved by meandering shape 52 of second heating element 42. Housing 16 of sensor 10, which is shown in a top view in FIG. 4 and is closed by lid diaphragm 50, has two diametrically opposed transverse sides 38 and two diametrically opposed longitudinal sides 36. Alternatively, it is also possible to implement housing 16 of sensor 10 in a circular cross section, which is closed by a lid diaphragm 50 and has an accordingly circular shape. According to this embodiment variation, one or more first heating elements 32 (compare illustration of FIG. 3) is/are located appropriately spaced on the outside of the mantle surface of a housing 16 implemented as a flat cylinder.

Both housing 16 and its side walls 34, as well as longitudinal side 36 and transverse side 38, may be heated from the outside, and a lid diaphragm 50 may also be heated by heating elements 32, 44 shown in FIGS. 2 through 4. Housing 16 and thus measuring chamber 14 are heated to an excess temperature which is significantly above the room temperature of 25° C., thus, for example, to an excess temperature T between 80° C. and 200° C. Correspondingly, measuring diaphragm 20 received on measuring chip 18 is heated to an excess temperature between 100° C. and 200° C., so that the relative humidity of gaseous fluid 26 within measuring chamber 14 is significantly reduced and the error attributed to the atmospheric moisture falls drastically. According to the achievement of the object of the present invention, the heat transmission no longer occurs at a temperature level between 20° C. and 120° C., but rather at a significantly higher temperature level between 120° C. and 220° C.

It is ensured by the higher temperature level within measuring chamber 14 that the influence of the atmospheric moisture of gaseous fluid 26 containing multiple components does not impair the detection of $H_2$ in gaseous fluid 26 and reliable detection of this component is possible.

What is claimed is:

1. A method for detecting a component in a gaseous fluid containing multiple components, using a sensor, which includes a measuring chamber delimited by a housing and a lid diaphragm, which allows the gaseous fluid to diffuse into the measuring chamber, the housing accommodating a heatable measuring element adapted to detect the component, the method comprising:
    heating the measuring chamber;
    wherein the component is $H_2$.

2. The method according to claim 1, wherein the measuring chamber is heated from an outside of the housing.

3. The method according to claim 1, wherein the measuring chamber is heated via at least one of (a) at least one side wall and (b) the lid diaphragm.

4. The method according to claim 1, further comprising heating the heatable measuring element to a temperature which is about 50 K to 200 K above a temperature level to which the housing is heated.

5. The method according to claim 4, further comprising heating the housing delimiting the measuring chamber to a temperature between 80° C. and 200° C.

6. The method according to claim 4, wherein the heatable measuring element is heated to a temperature between 100° C. and 200° C.

7. A sensor for detecting a component in a gaseous fluid containing multiple components, comprising:

a measuring chamber;

a heatable measuring element adapted to detect the component; and a housing and a lid diaphragm which delimit the measuring chamber, the housing accommodating the heatable measuring element, the housing having at least one first heating element, via which the measuring chamber is heated, the lid diaphragm allowing the gaseous fluid to diffuse into the measuring chamber;

wherein the component is $H_2$.

8. The sensor according to claim 7, wherein the lid diaphragm accommodates at least one second heating element.

9. The sensor according to claim 7, wherein the at least one first heating element is one of (a) integrated in a side wall of the housing and (b) applied to an external side of at least one side wall of the housing.

10. The sensor according to claim 8, wherein the heating elements are heating wires running in a meandering shape.

11. The sensor according to claim 8, wherein the heating elements include heating surfaces.

* * * * *